United States Patent [19]

Evans et al.

[11] Patent Number: 5,516,690

[45] Date of Patent: May 14, 1996

[54] **KETOPROFEN RESOLUTION BY ESTER HYDROLYSIS USING *TRICHOSPORON LAIBACCHII***

[75] Inventors: Chriatopher T. Evans, Heydon; Richard A. Wisdom, Cambridge, both of Great Britain; Peter J. Stabler, St. Meots, United Kingdom; Germano Carganico, Badalona, Spain

[73] Assignee: Laborabotios Menarini, S.A., Badalona, Spain

[21] Appl. No.: 193,004

[22] PCT Filed: Aug. 19, 1992

[86] PCT No.: PCT/EP92/01892

§ 371 Date: Jun. 17, 1994

§ 102(e) Date: Jun. 17, 1994

[87] PCT Pub. No.: WO93/04189

PCT Pub. Date: Mar. 4, 1993

[30] Foreign Application Priority Data

Aug. 22, 1991 [GB] United Kingdom ............ 9118149

[51] Int. Cl.$^6$ ............... C12P 41/00; C12P 7/40
[52] U.S. Cl. ............... 435/280; 435/136
[58] Field of Search ............... 435/280, 136

[56] References Cited

U.S. PATENT DOCUMENTS 5,322,791  6/1994  Sih ............... 435/280

FOREIGN PATENT DOCUMENTS 227078  1/1987  European Pat. Off. .

OTHER PUBLICATIONS

ATCC Catalogue of Yeasts pp. 95–96 (1990).

*Primary Examiner*—Marian C. Knode
*Assistant Examiner*—S. Saucier
*Attorney, Agent, or Firm*—Oblon, Spivak, McClelland, Maier & Neustadt

[57] ABSTRACT

Arylalkanoic acids are produced by biotransformation using suitable microorganisms and, in particular, (S)-ketoprofen in greater than 95% purity from racemic ketoprofen ethyl ester.

7 Claims, No Drawings

KETOPROFEN RESOLUTION BY ESTER HYDROLYSIS USING *TRICHOSPORON LAIBACCHII*

This application is a 371 of PCT EP92/01892 filed Aug. 19, 1992.

FIELD OF THE INVENTION

This invention relates to arylalkanoic acid resolution.

BACKGROUND OF THE INVENTION

Many pharmaceutically-active compounds produced by chemical synthesis are obtained and sold as mixtures of stereoisomers. However, it is often the case that only one these stereoisomers is pharmaceutically active. The contaminating enantiomer often has very poor, if any, activity or, in some instances, has unwanted physiological side-effects and shows toxicity.

Work by a number of researchers has shown that the anti-inflammatory activity of the 2-arylpropionic acids naproxen and ibuprofen is found with the (S) enantiomer. The same is true for ketoprofen, currently manufactured and sold as a racemate.

Arylalkanoic acids may be resolved by biotransformation, according to the following reaction scheme:

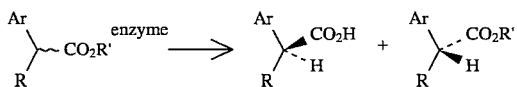

wherein R' is an alkyl group, Ar is an aromatic residue and, for example, R is an aliphatic residue of 1 to 4 carbon atoms.

One particular object behind the present invention is to provide an economic route to the production of optically pure (S)-ketoprofen.

SUMMARY OF THE INVENTION

The present invention provides, inter alia, a method for the resolution of (S)-ketoprofen from a racemic mixture. This method involves biocatalytic hydrolysis of an ester of racemic ketoprofen, to yield a biotransformation broth containing ketoprofen acid substantially enriched in one enantiomer and ketoprofen ester substantially enriched in the other enantiomer. Provided that the acid product of the biotransformation is sufficiently enriched with the desired enantiomer, further improvement of the optical purity can readily and economically be achieved using standard chemical procedures by forming a salt with a chiral amine of high optical purity, followed by crystallisation from solution. The residual ketoprofen ester from the biotransformation can readily be purified, chemically racemised and recycled for use in further biotransformations, to minimise raw material costs.

DESCRIPTION OF THE INVENTION

A preferred aspect of the present invention is based on the discovery of a biocatalyst suitable for use in the biotransformation described above: a microbe (ENZA-I3) has been identified that is extremely useful in carrying out the required resolution. This organism was originally isolated by screening samples from the sewage works for growth on ethanol as a sole source of carbon. Subsequent screening of the organism on plates containing ethyl ketoprofen showed that, following growth, there was extensive clearance of the non-water-soluble ethyl ketoprofen around ENZA-I3 colonies (indicative of potential ester hydrolysis). Subsequent screening in liquid media showed ENZA-I3 to be considerably more active at hydrolysing ethyl ketoprofen than other isolates during the liquid screen.

This strain has proved to have a number of characteristics advantageous for the resolution of (S)-ketoprofen from the racemic ketoprofen ester, as follows:

(a) It hydrolyses short-chain ketoprofen esters very rapidly.

It produces (S)-ketoprofen acid from racemic ethyl ketoprofen with very high enantioselectivity such that, at low conversions, greater than 95% purity (S)-ketoprofen can be obtained. At conversions approaching 50% (40–50%) this reduces to 90% purity. This selectivity is obtained without the need to purify out contaminating activities (which can be expensive) or over-express the activity of interest by cloning.

(c) By changing the substrate from ethyl to methyl ketoprofen it is possible to change the selectivity of the biocatalyst such that (R)-ketoprofen acid is preferentially accumulated instead of the (S) enantiomer. Thus, by taking the biotransformation to greater than 50%, (S)-ketoprofen can be produced as the methyl ester.

(d) The organism grows rapidly at ambient temperatures with a doubling time of 1.5 to 2 hours, enabling biocatalyst to be easily and economically prepared.

The isolated strain has been identified by Centralbureau Voor Schimmelcultures (CBS) in the Netherlands as *Trichosporon laibacchii* (Windisch) which is also classified as *Endomyces laibacchi*. Several alternative strains of this species are publicly available from the CBS. These strains, for instance CBS 5791, 5790, 5381 and 2495, have been obtained and tested alongside isolate ENZA-I3. These tests show that some of these strains are almost as good as isolate ENZA-I3 at carrying out the biotransformation. In the CBS 1990 catalogue ($32^{nd}$ edition), these strains are classified as *Trichosporon beigelii*, however they have subsequently been renamed by the CBS as *Endomyces laibacchii*. Strains of *T. beigelii* that have been tested have been found to have similar selectivity to ENZA-I3, although they are not as active.

ENZA-I3 has been deposited with the International Mycological Institute, Kew, UK on 20th Aug. 1991, under the terms of Budapest Treaty, where it has been given the accession number 348917.

Further characteristics of the deposited microbe ENZA-I3 are given below:

| Aerobic growth: | |
|---|---|
| D-Glucose | +ve |
| D-Galactose | +ve |
| L-Sorbose | +ve |
| D-Glucosamine | +ve |
| D-Ribose | +ve |
| D-Xylose | +ve |
| L-Arabinose | +ve |
| D-Arabinose | −ve |
| L-Rhamnose | +ve |
| Sucrose | +ve |
| Maltose | +ve |
| αα-Trehalose | +ve |
| Methyl α-glucoside | +ve |
| Cellobiose | +ve |
| Salicin | +ve |
| Arbutin | +ve |
| Melibiose | +ve |

| | |
|---|---|
| Lactose | +ve |
| Raffinose | +ve |
| Melezitose | +ve |
| Inulin | −ve |
| Soluble starch | +ve |
| Glycerol | +ve |
| Meso-erythritol | −ve |
| Ribitol | −ve |
| Xylitol | −ve |
| L-Arabinitol | +ve |
| D-Glucitol | +ve |
| D-Mannitol | −ve |
| Galactitol | +ve |
| Myoinositol | +ve |
| Gluconolactone | −ve |
| D-Gluconate | +ve |
| D-Glucuronate | +ve |
| D-Galacturonate | −ve |
| Di-lactate | +ve |
| Succinate | +ve |
| Citrate | +ve |
| Methanol | −ve |
| Ethanol | +ve |
| Use of nitrogen source: | |
| Nitrate | −ve on nitrate |
| Nitrite | −ve |
| Ethylamine | +ve |
| L-lysine | +ve |
| Cadaverine | +ve |
| Creatine | −ve |
| Creatinine | +ve |
| Growth: | +ve at 25° C., 30° C. |
| | −ve at 35° C., 37° C. |
| Appearance: | Colonies - cream, membranous |
| | Filaments - well-developed |
| | pseudohyphae/septae hyphae |
| | arthrocandida |
| | Asci - none |
| | Teliospores/basidia - none |

The following Examples illustrate the invention. The following media were used in Examples 1 to 5 (in which (S)-ketoprofen was produced):

| Component | Seed Medium (g/l) | Growth Medium (g/l) |
|---|---|---|
| Ammonium sulphate | 2 | 2 |
| Potassium dihydrogen | 10 | 10 |
| Magnesium sulphate 7H$_2$O | 0.5 | 0.5 |
| Yeast extract (Fould Springer) | 30 | 50 |
| Trace Elements | 1 ml/l | 1 ml/l |
| Antifoam (XFO 371)* | 1 ml/l | 1 ml/l |
| Glucose | — | 50 |

*Ivanhoe Chemical Company, IL, USA.

All media was adjusted to pH 6.5 with sodium hydroxide prior to autoclaving. All media were heat-sterilised at 121° C. for between 20 and 40 minutes prior to inoculation. The glucose was sterilised separately from the rest of the medium as a 50% solution.

The biotransformation mixture is as follows:

| | |
|---|---|
| Sodium phosphate | 100 mM, pH 6.5 |
| Yeast extract | 10 g/l |
| Tween 80 | 5 g/l |
| Antifoam (XFO 371) | 1 ml/l |

Ketoprofen ethyl ester was added to the biotransformation mixture, to give a final concentration of 50 g/l after the addition of the inoculum. The biotransformation medium was heat-sterilised at 121° C. for between 20 to 40 minutes; the ketoprofen ethyl ester was heat-sterilised separately.

The trace element solution used was as follows:

| | |
|---|---|
| CaCl$_2$.2H$_2$O | 3.57 g/l |
| ZnO | 2.0 g/l |
| CuCl$_2$.2H$_2$O | 0.85 g/l |
| Na$_2$MoO$_4$.2H$_2$O | 4.8 g/l |
| MnCl$_2$.4H$_2$O | 2.0 g/l |
| FeCl$_2$.6H$_2$O | 5.4 g/l |
| H$_3$BO$_3$ | 0.3 g/l |
| CoCl$_2$.6H$_2$O | 2.4 g/l |
| HCl | 250 ml/l |

EXAMPLE 1

Cells (ENZA-I3) were inoculated onto YM (Difco) agar plates and incubated at 23° C. for 2 days. A single colony was then transferred into 75 ml seed medium in a 500 ml shake flask. This was then grown aerobically at 23° C. for 24 hours. The culture was then transferred into a 2.8 l fermenter containing 1.5 l of growth medium at 23° C. Growth continued for 10 hours with sufficient aeration and stirring to maintain aerobic conditions. 150 ml of this culture was then transferred to 1.35 l biotransformation medium in a 2.8 l vessel. During the biotransformation, an agitation of 1200 rpm and an aeration of 0.5 vvm were maintained. The temperature was controlled at 23° C. A sample taken 20 hours after the start showed a ketoprofen concentration of 7 g/l with a purity of 98% (S)-ketoprofen. A sample taken 73 hours after the start of the biotransformation showed a ketoprofen concentration of 23.3 g/l with a purity of 94% (S)-ketoprofen.

EXAMPLE 2

A similar methodology to that described in Example 1 was used, but on a larger scale. Cells were inoculated onto YM (Difco) agar plates and incubated for 2 days. Single colonies were then transferred onto each of four, 1 l conical flasks containing 250 ml seed medium. After 1 day's growth, the contents of all flasks were transferred into a 15 l fermenter containing 9 l growth medium. After 0 hours' aerobic growth, 5 l of cell broth was transferred into a 75 l vessel containing 45 l biotransformation medium to start the biotransformation. An air flow rate of 0.2 vvm and an agitation rate of 500 rpm were used to maintain aerobic conditions and ensure good mixing. Analysis of a sample taken 71 hours after the start of the biotransformation showed that 17 g/l ketoprofen had been accumulated with a purity of 93% in favour of the (S) enantiomer.

EXAMPLE 3

Cultures of various strains available from CBS and shown in the following Table were transferred from fresh YM agar plates into 250 ml flasks containing 25 ml of growth medium without glucose. After 24 hours' growth, 5.0 ml of each culture was transferred into baffled 250 ml flasks containing 20 ml of biotransformation media. Samples were taken after shaking at 23° C. for 72 hours. The results are tabulated below:

| Strain | Ketoprofen formed (g/l) | % (S) Ketoprofen |
|---|---|---|
| ENZA-I3 *T. laibacchii* | 20 | 94 |
| CBS 5791 *T. laibacchii* | 17 | 93 |
| CBS 5790 *T. laibacchii* | 15 | 61 |

-continued

| Strain | Ketoprofen formed (g/l) | % (S) Ketoprofen |
| --- | --- | --- |
| CBS 5381 T. laibacchii | 13 | 93 |
| CBS 2495 T. laibacchii | 5 | —* |
| CBS 6858 Trichosporon Sp | <1 | —* |
| CBS 5959 T. beigelii | 1 | —* |
| CBS 2466 T. beigelii | <1 | —* |

*Difficult to quantify accurately due to low concentrations, but selectivity for the (S) enantiomer (to a greater or lesser extent) observed for strains.

Difficult to quantify accurately due to low concentrations, but selectivity for the (S) enantiomer (to a greater or lesser extent) observed for strains.

EXAMPLE 4

Effect of Temperature

Studies show that at 23 and 26° C. performance of the biocatalyst during the biotransformation is similar. At 20° C. the rate of biotransformation is similar to that at 23° C., but the enantioselectivity of the biocatalyst drops such that in a standard biotransformation (Example 1) the purity of the acid product is only 88% (S)-ketoprofen after 70 hours rather than 93–94%. At 30° C., the rate of catalysis falls by about 40–50% and the enantioselectivity is also not good.

EXAMPLE 5

Effect of pH

Activity is seen between pH 4.5 and 7.5 (and almost certainly higher though not tested). The selectivity of the biocatalyst decreases significantly below pH 4.5. The optimal pH is considered to be between 6.5 and 7.5.

Thus using the standard method (Example 1) with the pH controlled at 4.5, a sample at 66 hours had 8 g/l (purity 91% (S)-ketoprofen); at pH 6.5 after 66 hours, the sample had 24 g/l (purity 94%.(S)-ketoprofen); at pH 7.5 after 66 hours, the sample had 23 g/l (purity 80% (S)-ketoprofen).

EXAMPLE 6

Effect of Chain Length

Cells were grown in a medium containing 25 g/l yeast extract, 10 g/l potassium dihydrogen phosphate, 0.5 g/l magnesium sulphate heptahydrate, 2 g/l ammonium sulphate and 1 ml/l trace element solution. ($CaCl_2.2H_{20}$ O-53 g/l, $FeSO_4.7H_2O$-2 g/l, $ZnSO_4.H_2O$-100 mg/l, $AnSO_4.7H_2O$-200 mg/l $CuSO_4$-40 mg/l, $CoCl_2.6H_2O$-60 mg/l, $NaMoO_4$-40 mg/l, $H_3BO_3$-30 mg/l), with the pH adjusted to 6.5 with sodium hydroxide. After overnight growth, the cultures were transferred at 20° % into 250 ml baffled flasks containing 25 ml of the same medium, but with different ketoprofen esters added to 10 g/l final concentration. The rate of biotransformation and the enantiomeric purity of

| Ketoprofen Ester | Hydrolytic Relative Rate (%) | Purity |
| --- | --- | --- |
| Methyl | 70 | 86% (R)-ketoprofen |
| Ethyl | 100 | 93% (S)-ketoprofen |
| Butyl | 65 | 78% (S)-ketoprofen |
| Octyl | 38 | 54% (S)-ketoprofen |

We claim:

1. A process of preparing an enantiomer of 2-(3-benzoylphenyl)propionic acid from a mixture of (R) and (S) 2-(3-benzoylphenyl)propionic acid alkyl esters comprising:

combining a mixture of (R) and (S) 2-(3-benzoylphenyl)propionic acid alkyl esters with Trichosporon laibacchii;

hydrolyzing the ester of predominantly an enantiomer of said mixture; and recovering the enantiomer of 2-(3 -benzoylphenyl)propionic acid prepared.

2. The process of claim 1, wherein said Trichosporon laibacchii is Trichosporon laibacchii ENZA I-3 (IMI 348917).

3. The process of claim 1, wherein said alkyl esters of 2-(3-benzoylphenyl)propionic acid ester are methyl esters and the enantiomer prepared is (R) 2-(3-benzoylphenyl)propionic acid.

4. The process of claim 1, wherein said alkyl esters of 2-(3-benzoylphenyl)propionic acid ester are ethyl esters and the enantiomer prepared is (S) 2-(3-benzoylphenyl)propionic acid.

5. The process of claim 1, wherein said Trichosporon laibacchii is Trichosporon laibacchii CBS 5791, Trichosporon laibacchii CBS 5790, Trichosporon laibacchii CBS 5381 or Trichosporon laibacchii CBS 495.

6. The process of claim 1, wherein the pH of the hydrolysis reaction is from 4.5 to 7.5.

7. The process of claim 1, wherein the hydrolysis reaction is conducted at 20° to 30° C.

* * * * *

UNITED STATES PATENT AND TRADEMARK OFFICE
CERTIFICATE OF CORRECTION

PATENT NO. : 5,516,690
DATED : May 14, 1996
INVENTOR(S) : Christopher T. EVANS, et al.

It is certified that error appears in the above-indentified patent and that said Letters Patent is hereby corrected as shown below:

On the title page, in Item [75], the First Inventor's name should read:

--Christopher T. Evans--

Signed and Sealed this

Sixth Day of August, 1996

*Attest:*

BRUCE LEHMAN

*Attesting Officer*     *Commissioner of Patents and Trademarks*